United States Patent
Katayama et al.

(10) Patent No.: US 9,476,864 B2
(45) Date of Patent: *Oct. 25, 2016

(54) RADIOACTIVE GAS MONITOR

(71) Applicant: Mitsubishi Electric Corporation, Chiyoda-ku (JP)

(72) Inventors: Shohei Katayama, Tokyo (JP); Kenichi Moteki, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 450 days.

This patent is subject to a terminal disclaimer.

(21) Appl. No.: 14/455,492

(22) Filed: Aug. 8, 2014

(65) Prior Publication Data

US 2015/0276699 A1 Oct. 1, 2015

(30) Foreign Application Priority Data

Mar. 28, 2014 (JP) .................................. 2014-67444

(51) Int. Cl.
| | |
|---|---|
| *G01T 1/16* | (2006.01) |
| *G01N 33/00* | (2006.01) |
| *G01T 1/167* | (2006.01) |
| *G21C 17/00* | (2006.01) |
| *G21D 1/02* | (2006.01) |

(52) U.S. Cl.
CPC ........... *G01N 33/0055* (2013.01); *G01T 1/167* (2013.01); *G21C 17/00* (2013.01); *G21D 1/02* (2013.01); *Y02E 30/40* (2013.01)

(58) Field of Classification Search
CPC .. G01N 33/0055; G01T 1/167; G21C 17/00; G21D 1/02
See application file for complete search history.

(56) References Cited

U.S. PATENT DOCUMENTS

| | | | |
|---|---|---|---|
| 7,151,262 B1* | 12/2006 | Kitaguchi | ............... G01T 1/205 250/370.01 |
| 2005/0275545 A1* | 12/2005 | Alioto | ................... B66C 19/002 340/600 |
| 2014/0291530 A1* | 10/2014 | Moteki | ..................... G01T 1/16 250/366 |

FOREIGN PATENT DOCUMENTS

| | | |
|---|---|---|
| JP | 08-122443 A | 5/1996 |
| JP | 11-038143 A | 2/1999 |
| JP | 2001-153956 A | 6/2001 |
| JP | 2002-168957 A | 6/2002 |
| JP | 2005-009890 A | 1/2005 |
| JP | 4089522 B2 | 3/2008 |
| JP | 4453729 B2 | 2/2010 |

* cited by examiner

*Primary Examiner* — Casey Bryant
(74) *Attorney, Agent, or Firm* — Buchanan Ingersoll & Rooney PC

(57) ABSTRACT

A shield has a detector installing hole having a central axis orthogonal to a central axis of a detection tube. A radiation sensor of a columnar scintillation detector to which a low concentration side measurement range within all required measurement ranges is allocated is arranged inside the detector installing hole. An ionization chamber to which a high concentration side measurement range is allocated is arranged side by side in parallel with the detection tube. The measurement range of the columnar scintillation detector and the measurement range of the ionization chamber are adjusted so as to be overlapped with each other.

15 Claims, 13 Drawing Sheets

INNER DIAMETER OF DETECTION TUBE AND SENSITIVITY

FIG. 17

| TEMPERATURE | GAIN COMPENSATION COEFFICIENT |
|---|---|
| 10°C | 0.98 |
| ⋮ | ⋮ |
| 25°C | 1.0 |
| ⋮ | ⋮ |
| 50°C | 1.1 |
| ⋮ | ⋮ |
| 80°C | 1.2 |
| ⋮ | ⋮ |
| 100°C | 1.5 |
| ⋮ | ⋮ |
| 120°C | 1.6 |

RADIOACTIVE GAS MONITOR

BACKGROUND OF THE INVENTION

1. Field of the Invention

The present invention relates to a radioactive gas monitor which is installed in an exhaust pipe of nuclear facilities and which can measure radioactive concentration from an upper limit in a measurement concentration range of a normal time monitor to an upper limit in a measurement concentration range in response to severe accidents.

2. Description of the Related Art

In addition to a normal time gas monitor based on guidelines relating to measurement on emitted radioactive materials in power generating light water reactor facilities, an emergency-use gas monitor is disposed in an exhaust pipe of nuclear facilities in order to estimate the magnitude of a radioactive material amount emitted to the environment when a loss-of-coolant accident occurs in a nuclear reactor, based on examination guidelines relating to radiation measurement when the accident occurs in the power generating light water reactor facilities. The emergency-use gas monitor is designed so that an upper limit value in a measurement concentration range satisfies $3.7 \times 10^6 \mathrm{Bq/cm^3}$. In addition, a lower limit value in measurement is moderately overlapped with the upper limit value in measurement of the normal time gas monitor. However, in recent years, on the assumption of more severe accidents than the loss-of-coolant accident in the nuclear reactor, a gas monitor for coping with severe accidents whose temperature conditions are more stringent than those of the emergency-use gas monitor in the related art and whose measurement range is considerably expanded to a high concentration measurement side has been required.

As a preceding example in a method of expanding the measurement range to the high concentration measurement side, Patent Document 1 discloses a radioactive gas monitor which includes two sample containers having mutually different capacities, uses the large volume container as a low concentration measurement container, and uses the small volume container as a high concentration measurement container. In this example, the high concentration measurement container, a collimator, the low concentration measurement container, and a radiation detector are arrayed sequentially in this order, inside a shield. Flow is automatically switched over between a first sample container and a second sample container by an electromagnetic valve at a predetermined radiation measurement value.

Patent Document 2 discloses a radioactive concentration measurement apparatus in which a movable collimator having an inner diameter equivalent to that of the radiation detector is arranged between one sample container and the radiation detector. In this example, when the low concentration range is measured, the movable collimator is moved close to the radiation detector so as not to interfere with the measurement, and when the high concentration range is measured, the movable collimator is moved close to the sample container so as to narrow down the number of radioactive rays which are incident on the radiation detector per unit time.

[Patent Document 1] Japanese Patent No. 4453729
[Patent Document 2] Japanese Patent No. 4089522

In the sample container switching method disclosed in Patent Document 1, when flowing is switched over from the low concentration measurement container having the large volume to the high concentration measurement container having the small volume, a purge is performed on the low concentration measurement container arranged between the high concentration measurement container and the radiation detector. Consequently, there is a problem in that no measurement can be carried out during the purge.

In the movable collimator method disclosed in Patent Document 2, it is necessary to increase a moving distance of the movable collimator in order to expand a measurement range, thereby increasing a size of the shield. Furthermore, measurement results are unstable while the movable collimator is moving. Consequently, there is a problem in stability and responsiveness in a high concentration measurement range requiring a quick response. In addition, there is a problem in that a mechanism for moving the movable collimator is complicated, or there is a problem of increasing manufacturing cost since a precise stop position of the movable collimator is needed in order to improve measurement accuracy.

Furthermore, in recent years, in order to cope with severe accidents, a radioactive gas monitor has been required in which the upper limit value in the measurement concentration range satisfies $1 \times 10^{11} \mathrm{Bq/cm^3}$. However, the radioactive gas monitor is unlikely to be applied to the above-described sample container switching method or movable collimator method. That is, in the sample container switching method, it is necessary to allow the high concentration measurement container to have very small dimensions. In the movable collimator method, it is necessary to allow the collimator to have very large dimensions. Consequently, both methods are impractical since the manufacturing is difficult.

SUMMARY OF THE INVENTION

The present invention is made in view of the above circumstances, and an object thereof is to provide a radioactive gas monitor which can measure radioactive concentration in a wide range from a high concentration range for coping with severe accidents to a low concentration range measured by a normal time monitor, which is excellent in stability and responsiveness without causing time loss when the measurement range is switched over, and which can decrease a size of a shield.

A radioactive gas monitor according to an aspect of the present invention includes a detection unit that detects radiation emitted from radioactive nuclides contained in sample gas, and a measurement unit that processes a signal transmitted from the detection unit and outputs an engineering value corresponding to the radioactive concentration. The detection unit has a detection tube through which the sample gas flows, a first detector to which a low concentration side measurement range within all required measurement ranges is allocated, a second detector to which a high concentration side measurement range within all required measurement ranges is allocated, and a shield which shields the detection tube, the first detector, and the second detector from environmental radiation. The measurement unit has a first measurement unit which processes a signal transmitted from the first detector and a second measurement unit which processes a signal transmitted from the second detector. The shield has at least one detector installing hole having a central axis orthogonal to a central axis of the detection tube. At least the first detector between the first detector and the second detector is arranged inside the detector installing hole, and an inner diameter of the detection tube and a relative position between the detection tube and the first detector are determined so that the measurement ranges of the first detector and the measurement range of the second detector are overlapped with each other.

According to the radioactive gas monitor in the present invention, at least the first detector is arranged inside the detector installing hole disposed in the shield, and the measurement range of the first detector and the measurement range of the second detector are overlapped with each other. Therefore, the radioactive gas monitor can measure the radioactive concentration in a wide range from the high concentration range for coping with severe accidents to the low concentration range measured by a normal time monitor, and is excellent in stability and responsiveness without causing time loss when the measurement range is switched over. Furthermore, it is possible to decrease the size of the shield, thereby enabling cost reduction.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 17 illustrates a temperature compensation table in the radioactive gas monitor according to Embodiment 6 of the present invention.

DETAILED DESCRIPTION OF THE PREFERRED EMBODIMENTS

Embodiment 1

Figure 1:
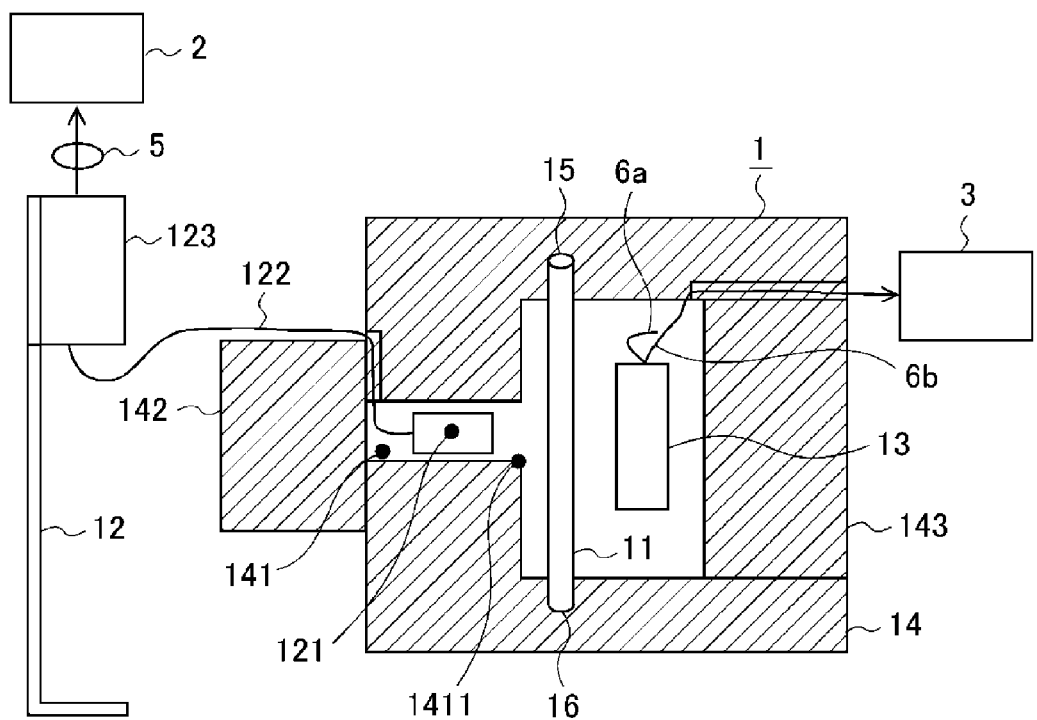
FIG. 1 is a cross-sectional view when a radioactive gas monitor according to Embodiment 1 of the present invention is laterally viewed.
Figure 2:
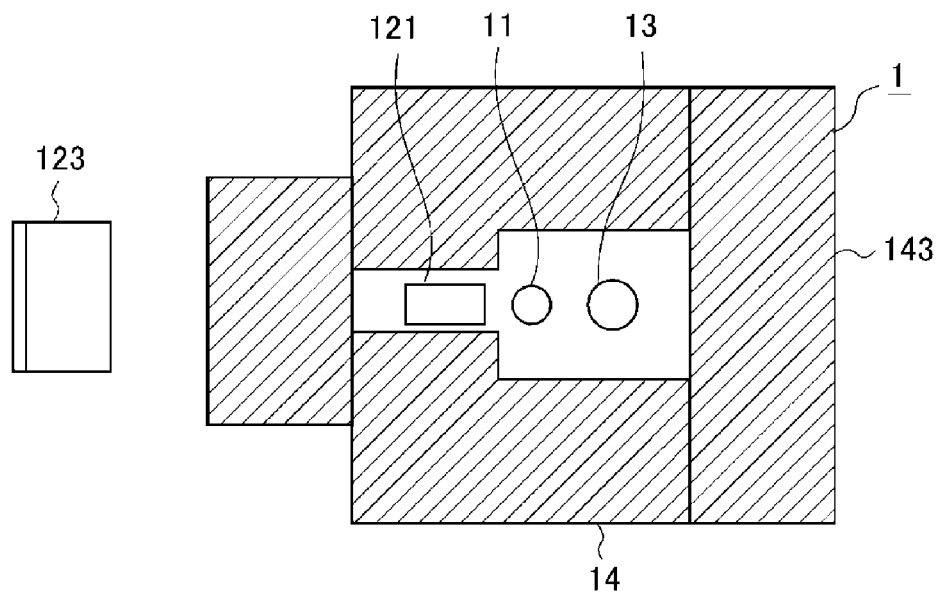
FIG. 2 is a cross-sectional view when the radioactive gas monitor according to Embodiment 1 of the present invention is viewed from above.

Hereinafter, a radioactive gas monitor according to Embodiment 1 of the present invention will be described with reference to the drawings. FIGS. 1 and 2 illustrate the radioactive gas monitor according to Embodiment 1. FIG. 1 is a cross-sectional view when laterally viewed, and FIG. 2 is a cross-sectional view when viewed from above. In the drawings, the same reference numerals are given to the same or equivalent elements.

The radioactive gas monitor according to Embodiment 1 includes, as main configuring elements, a detection unit 1 which detects radiation emitted from radioactive nuclides contained in sample gas, and a measurement unit which processes a signal transmitted from the detection unit 1 and outputs an engineering value corresponding to the radioactive concentration. The measurement unit has a low range measurement unit 2 serving as a first measurement unit and a high range measurement unit 3 serving as a second measurement unit.

The detection unit 1 includes a detection tube 11 through which the sample gas flows, a columnar scintillation detector 12 serving as a first detector to which a low concentration side measurement range within all required measurement ranges is allocated, a cylindrical ionization chamber 13 (hereinafter, abbreviated as an ionization chamber 13) serving as a second detector to which a high concentration side measurement range within all required measurement ranges is allocated, and a shield 14 which shields these from environmental radiation.

The shield 14 has a detector installing hole 141 having a central axis orthogonal to a central axis of the detection tube 11. A radiation sensor 121 of the columnar scintillation detector 12 is arranged inside the detector installing hole 141. In contrast, the ionization chamber 13 is arranged side by side in parallel with the detection tube 11. An inner diameter of the detection tube 11 and a relative position between the columnar scintillation detector 12 and the detection tube 11 are determined so that a measurement range of the columnar scintillation detector 12 and a measurement range of the ionization chamber 13 are overlapped with each other.

The shield 14 has a detector maintenance shield 142 and an ionization chamber maintenance shield 143, both of which are slidable during maintenance. When the columnar scintillation detector 12 is detached, the detector maintenance shield 142 is slid. Similarly, when the ionization chamber 13 is detached, the ionization chamber maintenance shield 143 is slid. A structure of the shield 14 is not limited thereto. For example, the ionization chamber maintenance shield 143 may be disposed in an upper portion thereof.

The sample gas is introduced into an intake nozzle 15 from an exhaust pipe by way of a sampling device, and is discharged from an exhaust nozzle 16 by way of the sampling device again. The introduced sample gas has a high temperature (for example, 200° C.) at a sampling point of the exhaust pipe. However, the sample gas is cooled down to approximately 150° C. in the middle of the pipe, if an ambient temperature is 100° C., for example.

The radiation sensor 121 of the columnar scintillation detector 12 absorbs energy of γ-rays emitted from radioactive nuclides contained in the sample gas inside the detection tube 11, and emits fluorescence having a light quantity proportional to the energy thereof. Furthermore, the radiation sensor 121 performs multiplication by converting the fluorescence into an electron, and outputs a current pulse having an electric charge amount proportional to the light quantity.

In order to perform the multiplication by converting the fluorescence into the electron, a high voltage is applied, as a bias, to the radiation sensor 121 from the low range measurement unit 2 by way of a coaxial cable included in a composite shielded cable 5, a preamplifier 123, and a detection cable 122.

The detection cable 122 superimposes the current pulse output from the radiation sensor 121 on the high voltage, and inputs the high voltage to the preamplifier 123. The preamplifier 123 extracts the current pulse superimposed on the high voltage by using a capacitor, and converts an analog current pulse thereof into an analog voltage pulse. The preamplifier 123 matches the analog voltage pulse with characteristic impedance of the coaxial cable included in the composite shielded cable 5, and transmits the analog voltage pulse to the low range measurement unit 2.

When a NaI (TI) scintillation detector is used as the columnar scintillation detector 12, it is possible to easily obtain the radiation sensor 121 which can be used in an environment of 150° C. The radiation sensor 121 is used in an intermediate temperature range between 150° C. of the maximum temperature in the sample gas and 100° C. of the maximum temperature in the ambient temperature. Therefore, the radiation sensor 121 is provided with a compensation function for the temperature, thereby being stably operated.

In contrast, the γ-rays emitted from the radioactive nuclides contained in the sample gas inside the detection tube 11 are incident on the ionization chamber 13. In this manner, the gas inside the ionization chamber 13 is ionized, the generated electric charge is collected to an electrode, and a minute DC current signal is output. In order to collect the electric charge generated inside the ionization chamber 13, a high voltage is applied to the ionization chamber 13 from the high range measurement unit 3 by way of a three-coaxial cable 6b for applying HV which serves as a bias.

The DC current signal output from the ionization chamber 13 is input to the high range measurement unit 3 by a three-coaxial cable 6a for outputting a signal current. The DC current signal output from the ionization chamber 13 has excellent temperature characteristics. Therefore, the ionization chamber 13 is stably operated even in the environment of a maximum of 200° C. without the compensation function being provided for the temperature. The three-coaxial cable 6a for outputting the signal current and the three-coaxial cable 6b for applying the HV can also be stably used at the temperature of 150° C. Accordingly, 100° C. of the maximum temperature in the ambient temperature is an affordable use condition.

Figure 3:
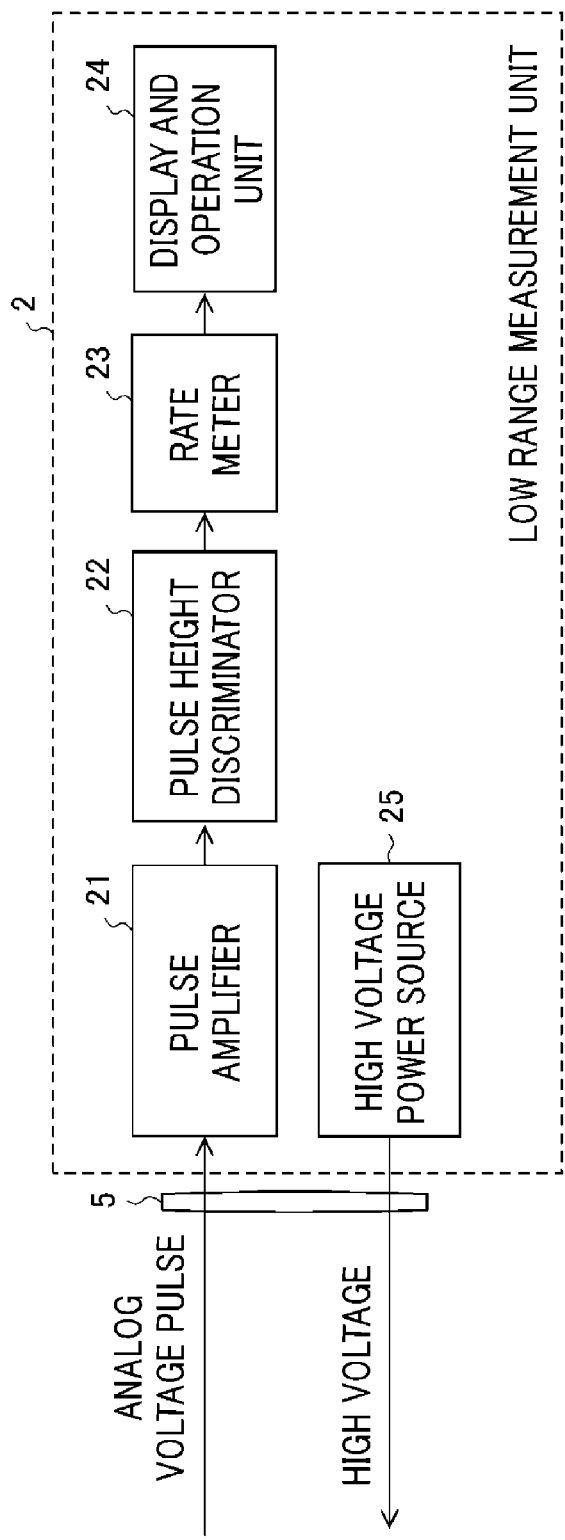
FIG. 3 illustrates a low range measurement unit of the radioactive gas monitor according to Embodiment 1 of the present invention.

The low range measurement unit 2 which processes the signal transmitted from the columnar scintillation detector 12 will be described with reference to FIG. 3. A pulse amplifier 21 amplifies the analog voltage pulse transmitted from the preamplifier 123 by way of the coaxial cable included in the composite shielded cable 5, and removes superimposed high frequency noises.

A pulse height discriminator 22 inputs the voltage pulse amplified by the pulse amplifier 21, outputs a digital pulse for the voltage pulse having a peak value satisfying a preset voltage level, and removes the other voltage pulse having the different peak value by regarding the other voltage pulse as a noise.

A rate meter 23 inputs the digital pulse transmitted from the pulse height discriminator 22, obtains a counting rate by performing a time constant process so that standard deviation is constant, for example, and outputs the counting rate as an engineering value. If necessary, the engineering value such as a dose equivalent rate may be output by multiplying the counting rate and a constant together.

A display and operation unit 24 displays the engineering value output from the rate meter 23, and performs required setting on a touch panel. A high voltage power source 25 generates a high voltage, and supplies the high voltage to the radiation sensor 121 via the coaxial cable included in the composite shielded cable 5 and the preamplifier 123.

A semiconductor component is used for the preamplifier 123. Types of the component are limited and there is a component having specifications suitable for high temperatures. If the preamplifier 123 having the specification suitable for high temperatures is selected and is installed outside the shield 14, the preamplifier 123 together with the detection cable 122 is stably operated under a use condition of 100° C. of the maximum temperature in the ambient temperature.

Figure 4:
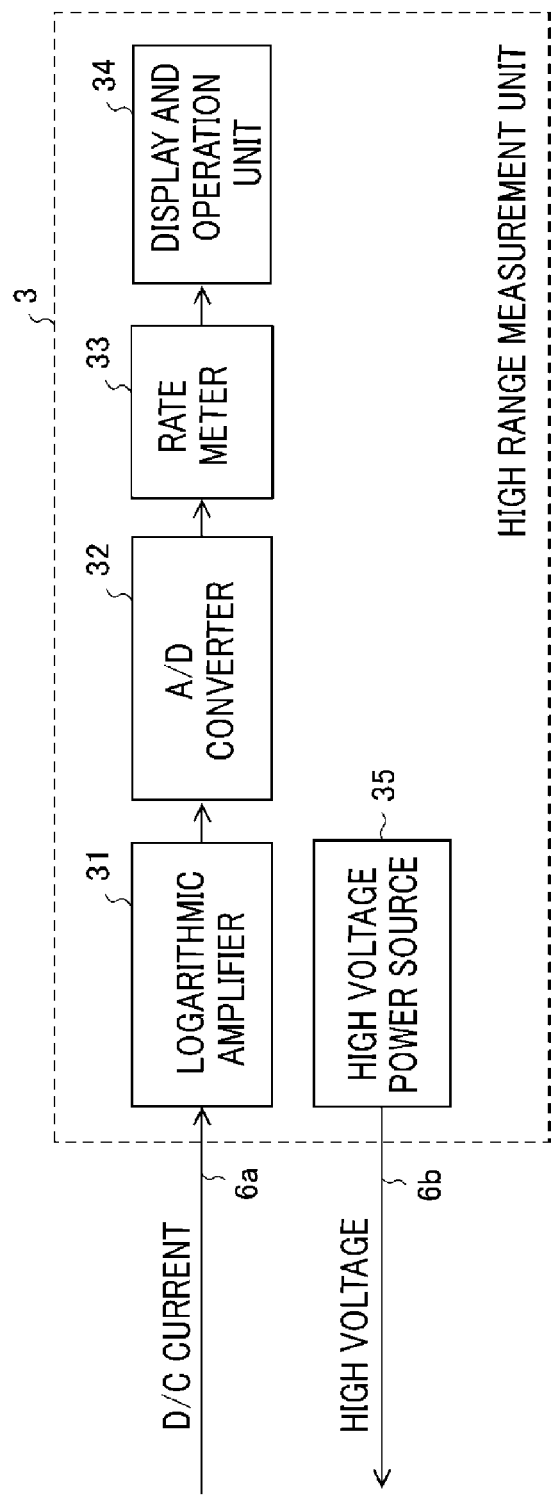
FIG. 4 illustrates a high range measurement unit of the radioactive gas monitor according to Embodiment 1 of the present invention.

Next, the high range measurement unit 3 which processes the DC current signal output from the ionization chamber 13 will be described with reference to FIG. 4. A logarithmic amplifier 31 inputs the DC current transmitted from the ionization chamber 13 by way of the three-coaxial cable 6a, and converts the DC current into the DC voltage proportional to a logarithm of the DC current.

An A/D converter 32 inputs the DC voltage output from the logarithmic amplifier 31, and converts the DC voltage into digital data. A rate meter 33 inputs the digital data transmitted from the logarithmic amplifier 31, converts the digital data into a current value, and outputs the current value as the engineering value, for example, as the dose equivalent rate. In addition, the current value may be output as it is.

A display and operation unit 34 displays the engineering value output from the rate meter 33, and performs required setting on a touch panel. The high voltage power source 25 generates a high voltage, and supplies the high voltage to the ionization chamber 13 via the three-coaxial cable 6b.

The logarithmic amplifier 31 performs logarithmic transformation of the output with respect to the input by utilizing the fact that the voltage between a base and an emitter of a transistor is proportional to the logarithm of the current. Measurement errors may occur due to the influence received from the ambient temperature. Therefore, the logarithmic amplifier 31 is not installed in the detection unit 1 whose maximum temperature is 100° C., but is installed in the high range measurement unit 3 which has an excellent temperature environment.

The output of the ionization chamber 13 is the DC current. The three-coaxial cable 6a serving as a transmission line is double-shielded, and has excellent noise immunity. Therefore, the output can be easily transmitted by using a cable length of approximately 300 m.

The measurement lower limit value of the columnar scintillation detector 12 is obtained by multiplying the counting rate defined as significant rising from a background, which is generally defined as three times the standard deviation of a background counting rate, that is, the counting rate (unit: cpm) and a detector calibration constant {unit: (Bg/cm$^3$)/cpm} together.

The measurement upper limit value of the columnar scintillation detector 12 is obtained by multiplying an upper counting rate (unit: cpm) defined as acceptable accuracy immediately before reaching a region where there is high probability that the analog pulses are piled up, and the influence thereof is not negligible, and the detector calibration constant {unit: (Bq/cm$^3$)/cpm} together.

During a periodic inspection of the radioactive gas monitor, the columnar scintillation detector 12 emits a standard ray source which is held in the nuclear reactor facilities, thereby performing single calibration to confirm soundness. In contrast, the ionization chamber 13 is not practical, since a highly intensive ray source is required when trying to obtain a significant output by emitting the standard ray source. Therefore, a less intensive α-ray source is incorporated into the ionization chamber 13, and it is checked whether a live zero current generated by emitting the α-ray source at all times does not significantly vary from an initial value (factory delivery value), thereby confirming the soundness.

Therefore, the measurement lower limit value of the ionization chamber 13 is obtained by multiplying the current defined as significant rising from the live zero current, which is generally defined as three times the standard deviation of the background current, that is, the current (unit: A) and the detector calibration constant {unit: (Bq/cm$^3$)/A} obtained as model calibration.

A saturation current value of a DC current output of the ionization chamber 13 is proportional to the square of a high voltage value (HV value) to be applied to the ionization chamber 13. Therefore, when the ionization chamber 13 is operated by a constant HV value being applied thereto, the measurement upper limit value of the ionization chamber 13 is defined regarding the current value having enough room for the saturation current value of the HV value as the measurement upper limit value of the ionization chamber 13. In this manner, the ionization chamber 13 is stably operated in a region of excellent plateau characteristics. The measurement upper limit value of the ionization chamber 13 is obtained by multiplying the saturation current value (unit: A) and the detector calibration constant {unit: (Bq/cm$^3$)/A}.

The measurement range required for the radioactive gas monitor according to Embodiment 1 is in a range up to $1\times10^{11}$ Bq/cm$^3$ of the measurement upper limit concentration required for severe accidents, since the measurement range is overlapped by approximately a half decade with the upper limit concentration for which the normal time gas monitor regulated by the guidelines relating to the measurement of the emitted radioactive materials in the power generating light water reactor facilities is responsible.

That is, it is necessary to unceasingly satisfy all the measurement ranges from the measurement range (for example, $2\times10^{-3}$ Bq/cm$^3$ to $1\times10^2$ Bq/cm$^3$) of the normal time gas monitor corresponding to the above-described measurement guidelines to the measurement range to the upper limit measurement value $1\times10^{11}$ Bq/cm$^3$ (for example, $2\times10^1$ Bq/cm$^3$ to $1\times10^{11}$ Bq/cm$^3$) of the exhaust pipe gas monitor for severe accidents.

The reciprocal of the measurable concentration upper limit corresponds to the sensitivity of the detector. Accordingly, if the reciprocal is defined as the sensitivity for the sake of convenience, the columnar scintillation detector 12 has the sensitivity which is higher than that of the ionization chamber 13 by several decades. For this reason, the columnar scintillation detector 12 and the ionization chamber 13 form a suitable combination to cover the measurement range from the low range to the high range. However, if the columnar scintillation detector 12 and the ionization chamber 13 are simply arranged around the detection tube 11, either the upper limit value or the lower limit value of the measurement range, or alternatively both of these have an insufficient range.

Therefore, in Embodiment 1, the ionization chamber 13 having the sensitivity suitable for an inner diameter of the detection pipe 11 is first selected so that the ionization chamber 13 satisfies the required high concentration side measurement range. Then, dimensions of the columnar scintillation detector 12 which are suitable for the inner diameter of the detection pipe 11 are determined so that the columnar scintillation detector 12 satisfies the required low concentration side measurement range, and the radiation incident on the columnar scintillation detector 12 is adjusted. The columnar scintillation detector 12 is selected from among those which have dimensions allowing the sensitivity of approximately four or five times (approximately four times is preferable) the sensitivity of the ionization chamber 13.

In Embodiment 1, as specific adjusting means, the detector installing hole 141 is disposed in the shield 14, and the radiation sensor 121 of the columnar scintillation detector 12 is arranged thereinside. Furthermore, with respect to a window 1411 through which the detection tube 11 is viewed from the inside of the detector installing hole 141, a relative position of the radiation sensor 121 and the detection tube 11 is adjusted, and an amount of the radiation incident on the radiation sensor 121 is adjusted.

If the detection tube 11 is moved close to the window 1411, the detection tube 11 is poorly visible from the columnar scintillation detector 12. Consequently, the amount of the incident radiation decreases. On the other hand, if the detection tube 11 is moved away from the window 1411, the amount of the incident radiation increases. The adjustment of the relative position optimizes the overlapped measurement range between the ionization chamber 13 and the columnar scintillation detector 12.

In Embodiment 1, a specific procedure for allocating the measurement range to the ionization chamber 13 and the columnar scintillation detector 12 will be described with reference to FIG. 5. In the following description, the ionization chamber 13 is represented by those which are generally available and in which the dose equivalent rate measurement range is $5\times10^{-5}$ Sv/h to $1\times10^1$ Sv/h. In addition, an NaI (Tl) scintillation detector is used as the columnar scintillation detector 12, and the counting rate measurement range is set to $1\times10^1$ cpm to $1\times10^7$ cpm which is generally used.

Figure 5:
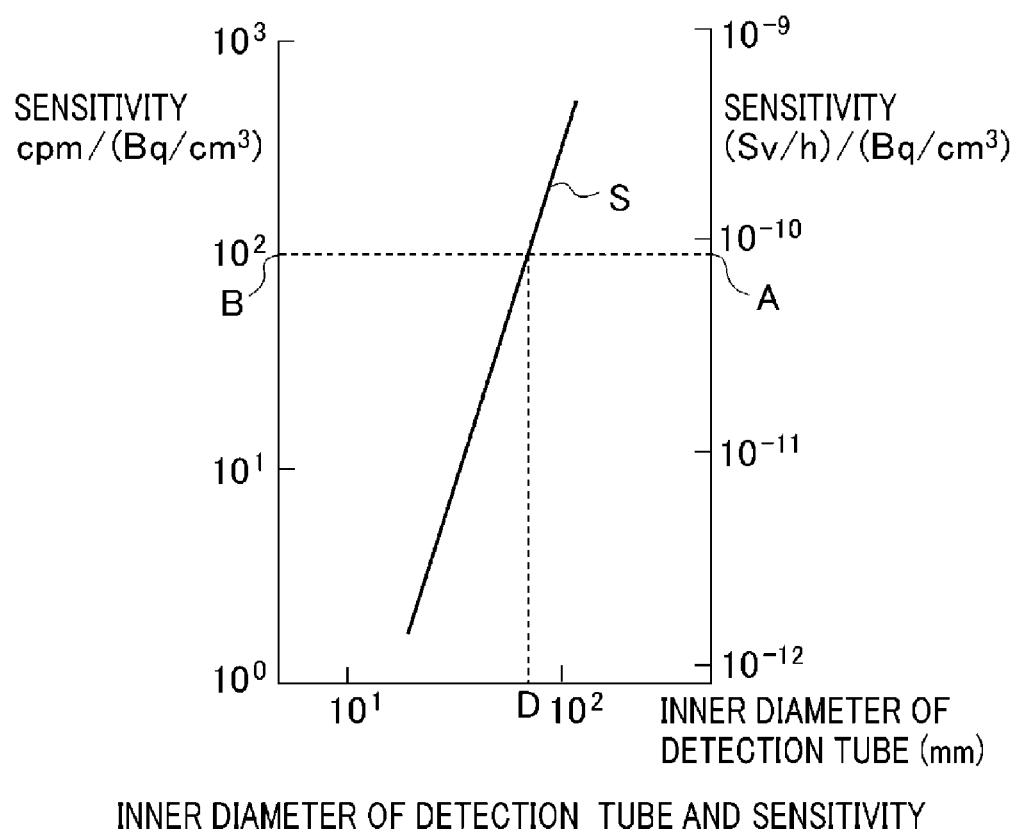
FIG. 5 illustrates a relationship between an inner diameter of a detection tube and sensitivity in the radioactive gas monitor according to Embodiment 1 of the present invention.

A graph S illustrated in FIG. 5 is first prepared by setting parameters where an inner diameter (mm) of the detection tube 11 having a predetermined length which is approximately two times the length of the ionization chamber 13 is a horizontal axis, and where sensitivity cpm/(Bq/cm$^3$) of the columnar scintillation detector 12 of the detection unit 1 which is calculated or obtained by actual measurement and sensitivity (Sv/h)/(Bq/cm$^3$) of the ionization chamber 13 are vertical axes.

With respect to sensitivity $1\times10^{-10}$ (Sv/h)/(Bq/cm$^3$) when the measurement range upper limit dose equivalent rate ($1\times10^1$ Sv/h) of the ionization chamber 13 in the graph S corresponds to the required measurement concentration upper limit ($1\times10^{11}$ Bq/cm$^3$), based on an intersecting point between sensitivity A securing slight room for the sensitivity and the graph S, an inner diameter D of the detection tube 11 and sensitivity B corresponding to the sensitivity A are tentatively determined.

Subsequently, ionization chamber upper limit concentration C4 is tentatively determined by dividing the measurement range upper limit dose equivalent rate of the ionization chamber 13 by the sensitivity A. Furthermore, ionization chamber lower limit concentration C3 is tentatively determined by dividing the measurement range lower limit dose equivalent rate ($5 \times 10^{-5}$ Sv/h) of the ionization chamber 13 by the sensitivity A.

Next, columnar scintillation detector upper limit concentration C2 is obtained by dividing the measurement upper limit counting rate ($1 \times 10^7$ cpm) of the columnar scintillation detector 12 by the sensitivity B. For example, when increased ambient radiation during the accident causes the background of the columnar scintillation detector 12 to be raised by 10 cpm, and when 10 cpm is equivalent to three time the standard deviation of the background counting rate, columnar scintillation detector lower limit concentration C1 is obtained by dividing 10 cpm by the sensitivity B.

When a head of the radiation sensor 121 of the columnar scintillation detector 12 is located, for example, at a surface position of the window 1411, if C1 satisfies the required lower limit concentration but a relationship is C2<C3, the measurement range of the ionization chamber 13 and the measurement range of the columnar scintillation detector 12 are not overlapped with each other. In this case, fine adjustment is performed by lowering the head rearward from the window 1411. For example, tentative determination is made so that the measurement ranges are overlapped with each other by approximately 0.3 decades.

In addition, when the relationship is C2>C3 and the measurement ranges are moderately overlapped with each other, but if C1 has a significantly insufficient range as compared to the required lower limit concentration, the detection tube 11 is moved close to the window 1411 to widen a field of view for the columnar scintillation detector 12. Furthermore, in some cases, fine adjustment is performed so that the head of the columnar scintillation detector 12 is slightly protruded from the window 1411. For example, tentative determination is made so that the measurement ranges are overlapped with each other by approximately 0.3 decades.

The adjustment is performed as described above. In this manner, the tentative determination becomes final determination by confirming whether both of the measurement range of the columnar scintillation detector 12 and the measurement range of the ionization chamber 13 satisfy the required range, and whether the respective measurement ranges are moderately overlapped with each other.

Figure 6:
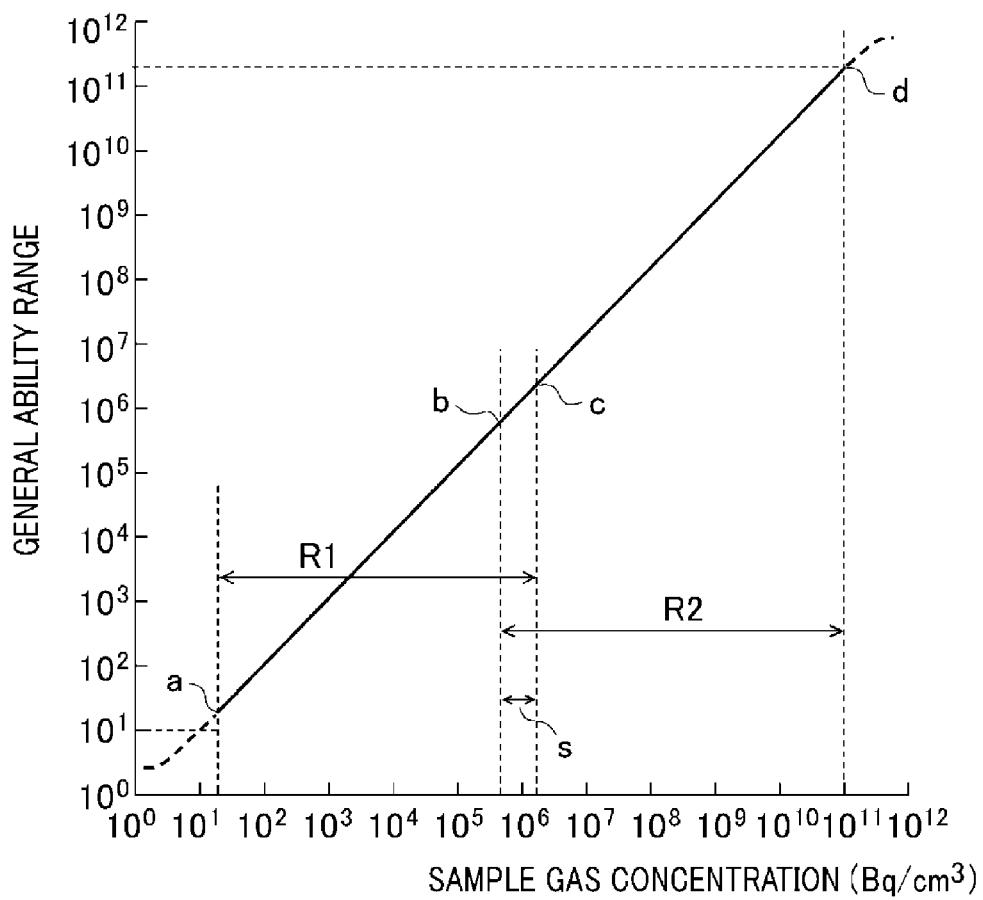
FIG. 6 illustrates distribution of a measurement range in the radioactive gas monitor according to Embodiment 1 of the present invention.

FIG. 6 illustrates range distribution finely adjusted in the manner described above. The horizontal axis represents sample gas concentration (Bq/cm$^3$), and the vertical axis represents a general ability range. In FIG. 6, marks a to c represent the low concentration side measurement range (R1) allocated to the columnar scintillation detector 12, and marks b to d represent the high concentration side measurement range (R2) allocated to the ionization chamber 13. A mark s represents overlapping between the respective measurement ranges R1 and R2.

As described above, according to the radioactive gas monitor in Embodiment 1, the detector installing hole 141 is disposed in the shield 14, and the radiation sensor 121 of the columnar scintillation detector 12 is arranged inside the detector installing hole 141 so that the measurement range of the ionization chamber 13 and the measurement range of the columnar scintillation detector 12 are overlapped with each other. Therefore, it is possible to measure the wide range from the upper limit value of the measurement concentration range corresponding to the normal time monitor and to the upper limit of the measurement concentration range corresponding to severe accidents.

In addition, there is no time loss when the measurement ranges are switched over to each other. Accordingly, the radioactive gas monitor is excellent in stability and responsiveness. Furthermore, it is possible to decrease the size of the shield 14 as the overall detection unit 1 by disposing the detector installing hole 141 in the shield 14, thereby enabling cost reduction.

Embodiment 2

Figure 7:
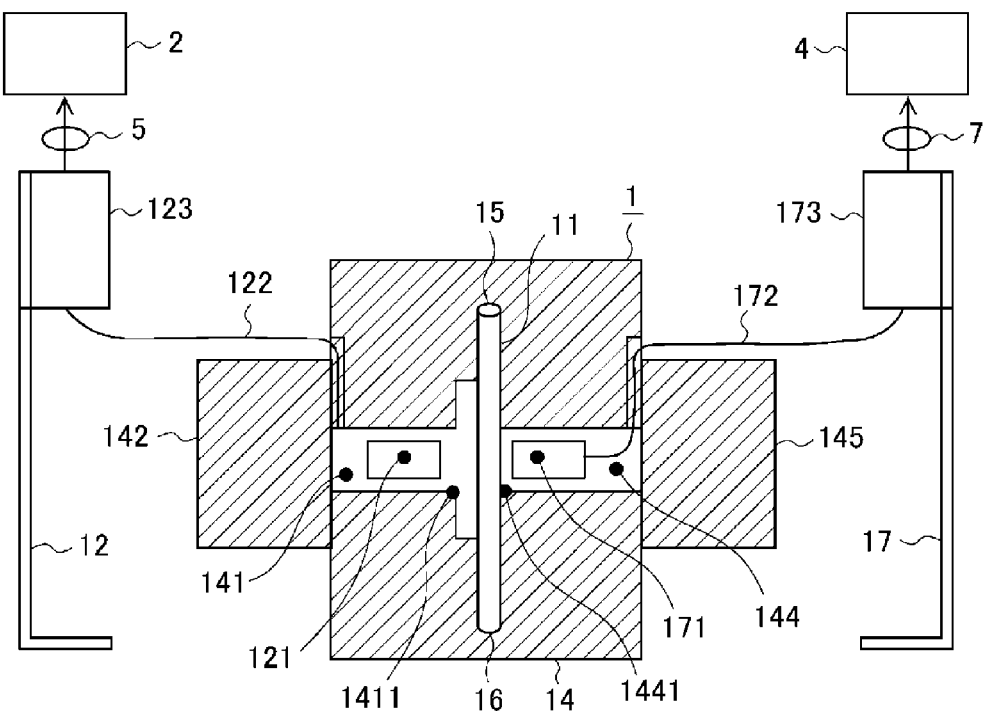
FIG. 7 is a cross-sectional view when a radioactive gas monitor according to Embodiment 2 of the present invention is laterally viewed.
Figure 8:
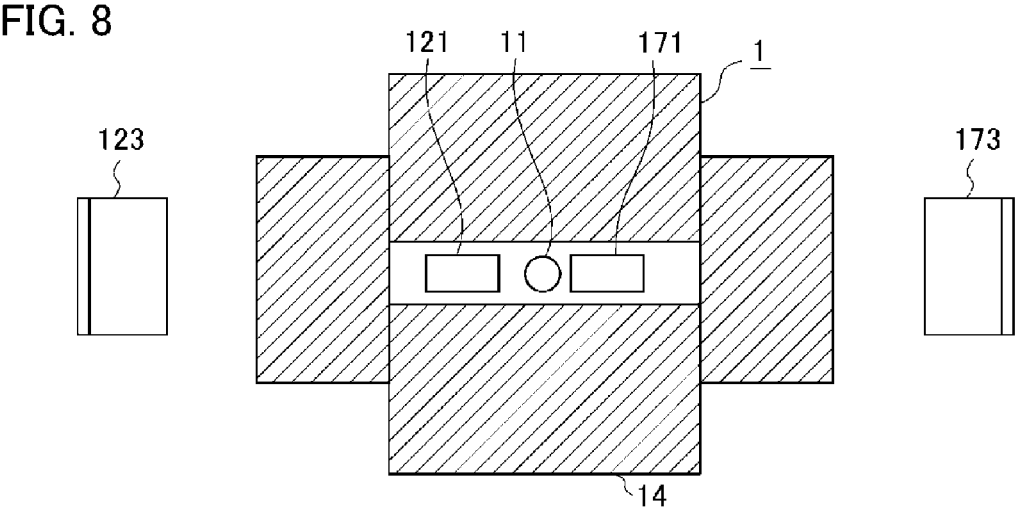
FIG. 8 is a cross-sectional view when the radioactive gas monitor according to Embodiment 2 of the present invention is viewed from above.

FIGS. 7 and 8 illustrate a radioactive gas monitor according to Embodiment 2 of the present invention. FIG. 7 is a cross-sectional view when laterally viewed, and FIG. 8 is a cross-sectional view when viewed from above. In FIG. 7, the same reference numerals are given to the same or equivalent elements in FIG. 1, and description thereof will be omitted.

In Embodiment 1 described above, the ionization chamber 13 is used as the second detector to which the high concentration side measurement range within all the required measurement ranges is allocated. However, in Embodiment 2, a fibrous scintillation detector 17 is used. A high range measurement unit 4 processes a signal transmitted from the fibrous scintillation detector 17.

Similar to the columnar scintillation detector 12, the fibrous scintillation detector 17 includes a radiation sensor 171 which emits fluorescence when the radiation is detected, and which outputs a current pulse by converting the fluorescence into an electron, a preamplifier 173 which converts the current pulse into an analog voltage pulse, and a detector cable 172 which inputs the current pulse transmitted from the radiation sensor 171 to the preamplifier 173.

Figure 9:
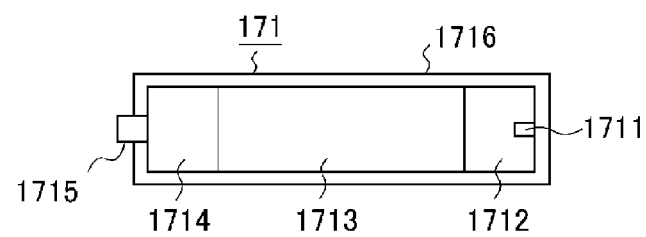
FIG. 9 illustrates a fibrous scintillation detector of the radioactive gas monitor according to Embodiment 2 of the present invention.

FIG. 9 illustrates the radiation sensor 171 of the fibrous scintillation detector 17. The radiation sensor 171 is obtained in such a manner that a scintillation fiber 1711 cut out to have a length determined based on preceding experiments is inserted into and optically bonded to a light guide 1712, and further a photomultiplier tube 1713 is optically bonded to the light guide 1712.

The scintillation fiber 1711 absorbs energy of γ-rays emitted from radioactive nuclides contained in the sample gas inside the detection tube 11, and emits the fluorescence having a light quantity proportional to the energy thereof. For example, as the scintillation fiber 1711, a glass scintillation fiber can be used in the environment of 150° C. Those which have a small diameter of 0.5 mm or less are readily available.

The photomultiplier tube 1713 converts the fluorescence into the electron, multiplies the electron, and outputs the current pulse having an electric charge amount proportional to the light quantity. A distribution circuit 1714 divides the high voltage supplied from a high voltage power source 45 of the high range measurement unit 4, and distributes the divided high voltage as a bias in order to operate the photomultiplier tube 1713.

Figure 10:
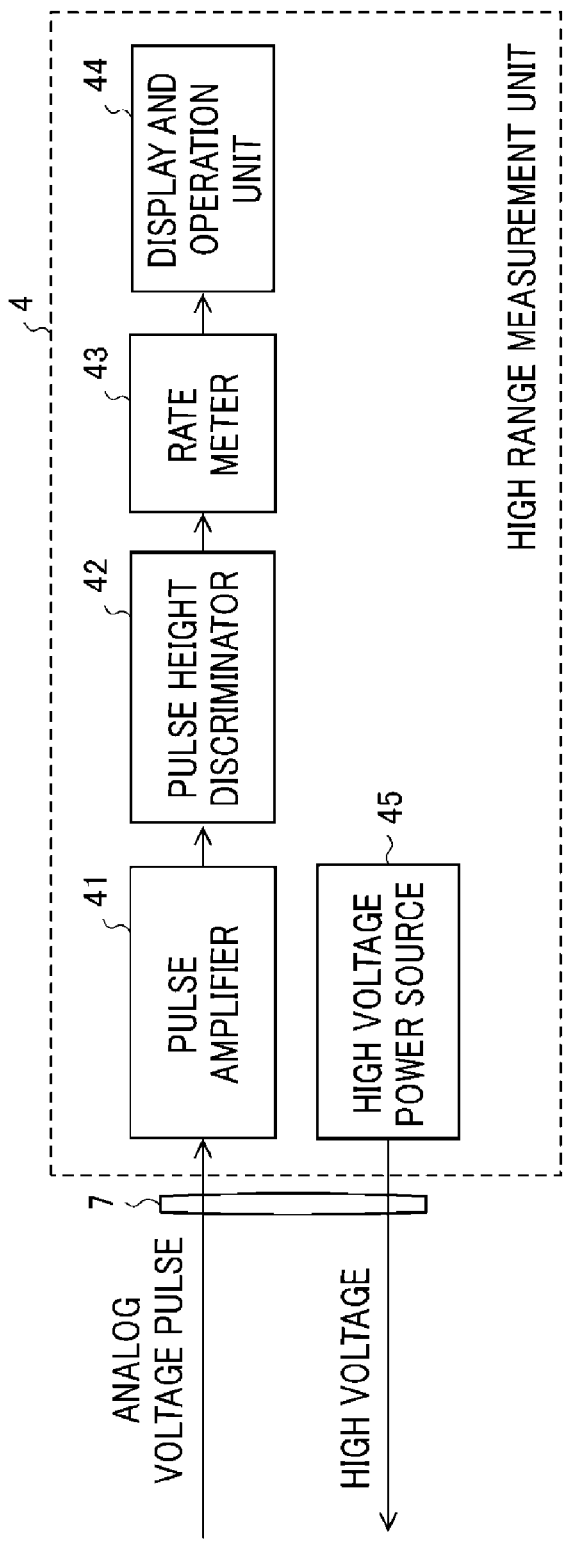
FIG. 10 illustrates a high range measurement unit of the radioactive gas monitor according to Embodiment 2 of the present invention.

The high range measurement unit 4 which processes the signal transmitted from the fibrous scintillation detector 17 will be described with reference to FIG. 10. A pulse amplifier 41 amplifies an analog voltage pulse transmitted from the preamplifier 173 by way of a coaxial cable included in a composite shielded cable 7, and removes superimposed high frequency noises.

A pulse height discriminator 42 inputs the voltage pulse amplified by the pulse amplifier 41, outputs a digital pulse for the voltage pulse having a peak value satisfying a preset voltage level, and removes the other voltage pulse having the different peak value by regarding the other voltage pulse as a noise.

A rate meter 43 inputs the digital pulse transmitted from the pulse height discriminator 42, obtains a counting rate by performing a time constant process so that the standard deviation is constant, for example, and outputs the counting rate as an engineering value. If necessary, the engineering value such as the dose equivalent rate may be output by multiplying the counting rate and a constant together.

A display and operation unit 44 displays the engineering value output from the rate meter 43, and performs required setting on a touch panel. The high voltage power source 45 generates a high voltage, and supplies the high voltage to the radiation sensor 171 via the coaxial cable included in the composite shielded cable 7 and the preamplifier 173.

In Embodiment 2, as illustrated in FIG. 7, the shield 14 has two detector installing holes 141 and 144 which are arranged so as to oppose each other across the detection tube 11. The radiation sensor 121 of the columnar scintillation detector 12 is arranged inside the detector installing hole 141, and the radiation sensor 171 of the fibrous scintillation detector 17 is arranged inside the other detector installing hole 144.

The central axis of the detector installing holes 141 and 144 is orthogonal to the central axis of the detection tube 11. In addition, the shield 14 has a detector maintenance shield 145 which is slidable during maintenance. When the fibrous scintillation detector 17 is removed, the detector maintenance shield 145 is slid.

In Embodiment 2, an inner diameter of the detection tube 11 and a relative position between the columnar scintillation detector 12 and the detection tube 11 are determined so that the measurement range of the columnar scintillation detector 12 and the measurement range of the fibrous scintillation detector 17 are overlapped with each other. A head of the radiation sensor 171 of the fibrous scintillation detector 17 is arranged close to a window 1441 through which the detection tube 11 is visible from the inside of detector installing hole 144.

In addition, a head of the radiation sensor 121 of the columnar scintillation detector 12 is caused to have a sensitive area which is smaller by approximately four decades than that in Embodiment 1 described above. Furthermore, visibility for the detection tube 11 is caused to be smaller by approximately one decade. This enables the ionization chamber 13 in Embodiment 1 described above to be replaced by the fibrous scintillation detector 17.

According to Embodiment 2, an advantageous effect which is the same as that in Embodiment 1 described above can be obtained. It is possible to decrease the size of the shield 14 as the overall detection unit 1, thereby further enabling cost reduction.

Embodiment 3

A radioactive gas monitor according to Embodiment 3 of the present invention is configured so that in the radioactive gas monitor similar to that in Embodiment 1 or Embodiment 2 described above, a collimator 146 for narrowing down the radiation incident on the radiation sensors 121 and 171 is disposed inside the detector installing holes 141 and 144 disposed in the shield 14. The other configurations are the same as those in Embodiment 1 or Embodiment 2 described above. Therefore, the different configuration will be described using FIG. 1.

For example, when the measurement range of the columnar scintillation detector 12 is suitably arranged, if only a distance of the head of the radiation sensor 121, the window 1411, and the detection tube 11 is adjusted, a wide space is required inside the shield 14.

Figure 11:
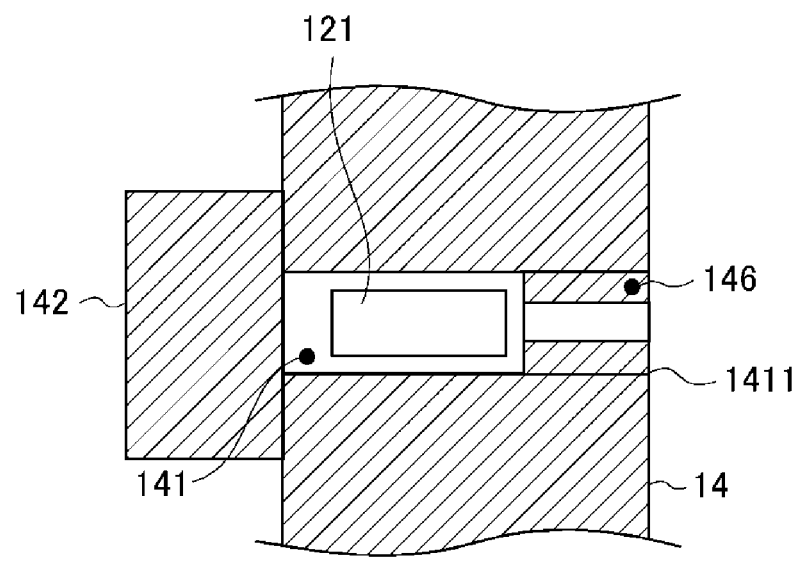
FIG. 11 illustrates a collimator of a radioactive gas monitor according to Embodiment 3 of the present invention.

Therefore, in Embodiment 3, as illustrated in FIG. 11, the collimator 146 is disposed near the window 1411 through which the detection tube 11 of the detector installing hole 141 is visible, thereby narrowing down the incident radiation. In FIG. 11, the detector installing hole 141 in which the radiation sensor 121 of the columnar scintillation detector 12 is arranged thereinside. However, the collimator can also be similarly disposed in the detector installing hole 144 (refer to FIG. 7).

According to Embodiment 3, an advantageous effect which is the same as those in Embodiment 1 and Embodiment 2 which are described above can be obtained. Without widening the internal space of the shield 14, it is possible to more preferably arrange the measurement range so as to be suitable. Therefore, it is possible to further decrease the size of the shield 14.

Embodiment 4

In Embodiment 4 of the present invention, the detection unit 1 of the radioactive gas monitors according to Embodiment 1 to Embodiment 3 includes a sample gas temperature sensor 112 which detects a temperature of the sample gas flowing in the detection tube 11 and a sample gas pressure sensor 113 which detects a pressure of the sample gas flowing in the detection tube 11.

Figure 12:
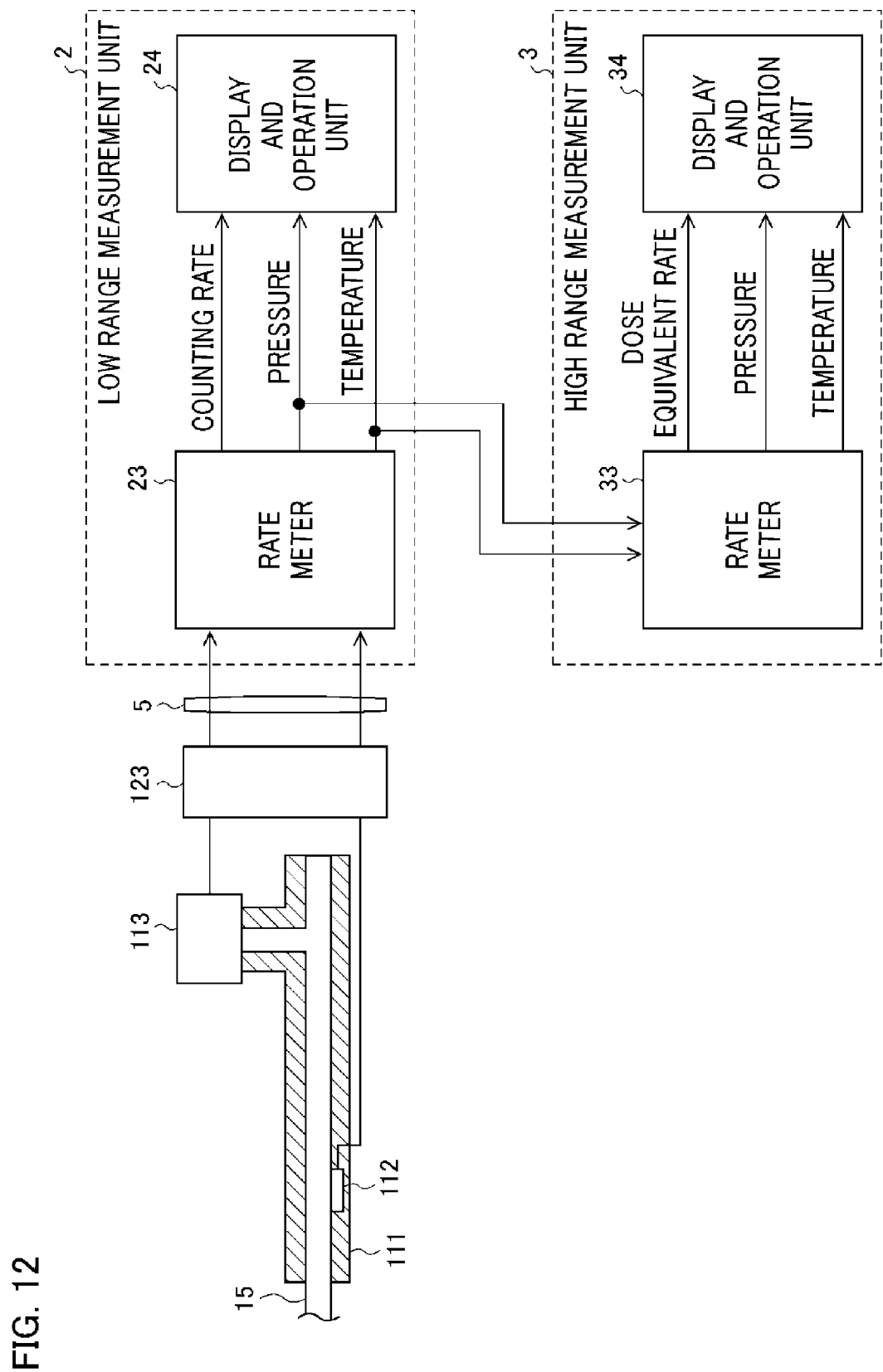
FIG. 12 illustrates a radioactive gas monitor according to Embodiment 4 of the present invention.

FIG. 12 illustrates a radioactive gas monitor according to Embodiment 3. In FIG. 12, the same reference numerals are given to the same or equivalent elements in FIGS. 1 to 4. For example, the sample gas temperature sensor 112 is a resistance temperature detector, and is attached to a surface of the intake nozzle 15. An insulation material 111 is disposed on the surface of the intake nozzle 15, and thus, the sample gas temperature sensor 112 is thermally insulated from the surrounding.

The sample gas temperature sensor 112 may be attached by being brought into contact with the detection tube 11 at a position and an angle which do not interfere with the radiation measurement. In this case, the insulation material 111 is not required. In addition, the sample gas pressure sensor 113 is attached to a portion branched from the intake nozzle 15.

The low range measurement unit 2 inputs a temperature signal transmitted from the sample gas temperature sensor 112 and a pressure signal transmitted from the sample gas pressure sensor 113 to the rate meter 23. Based on the signals, the low range measurement unit 2 calculates and outputs the sample gas temperature and pressure.

Furthermore, the sample gas temperature and pressure which are obtained by the low range measurement unit 2 are input to the rate meter 33 of the high range measurement unit 3, and are output to the display and operation units 24 and 34, if necessary. In FIG. 12, the high range measurement unit 3 (refer to FIG. 4) according to Embodiment 1 described above is illustrated. However, the high range measurement unit 4 (refer to FIG. 10) in Embodiment 2 described above also has the same configuration.

According to Embodiment 4 of the present invention, an advantageous effect the same as those in Embodiment 1 to Embodiment 3 can be obtained. It is possible to obtain information for manually converting an engineering value corresponding to radioactive concentration into a value of a reference temperature and pressure.

Embodiment 5

In Embodiment 5, in the radioactive gas monitor according to Embodiment 4 described above, the low range measurement unit 2 and the high range measurement units 3 and 4 are provided with a function which outputs the value by automatically converting the engineering value corresponding to the radioactive concentration into the value of the reference temperature and pressure, based on the sample gas temperature and pressure.

Figure 13:
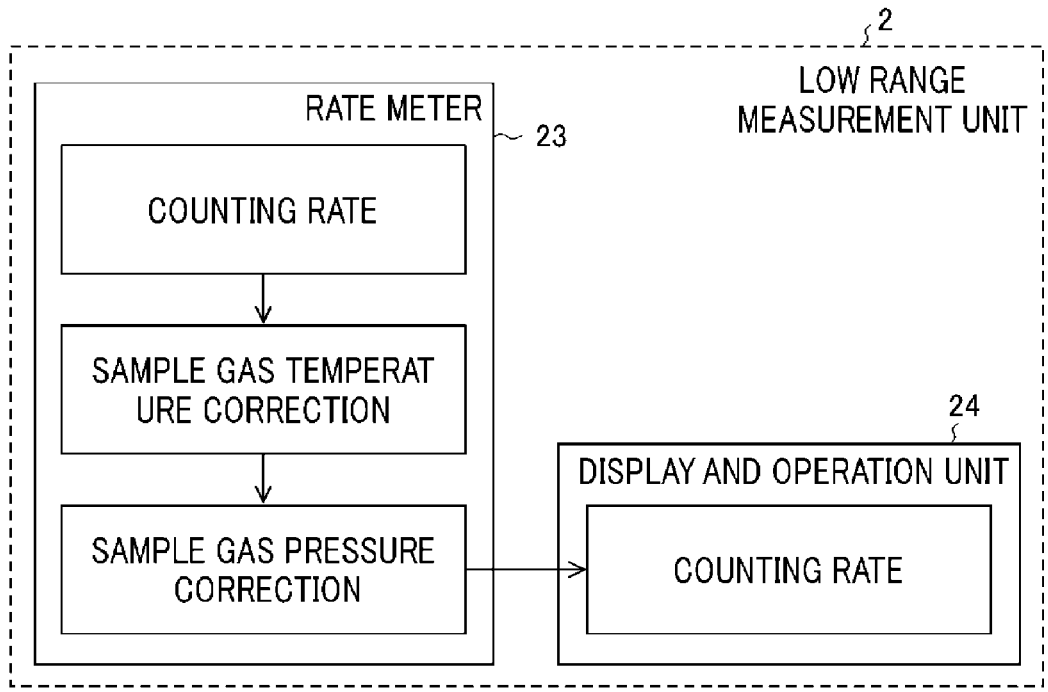
FIG. 13 illustrates a flowchart of an operation in a low range measurement unit of a radioactive gas monitor according to Embodiment 5 of the present invention.
Figure 14:
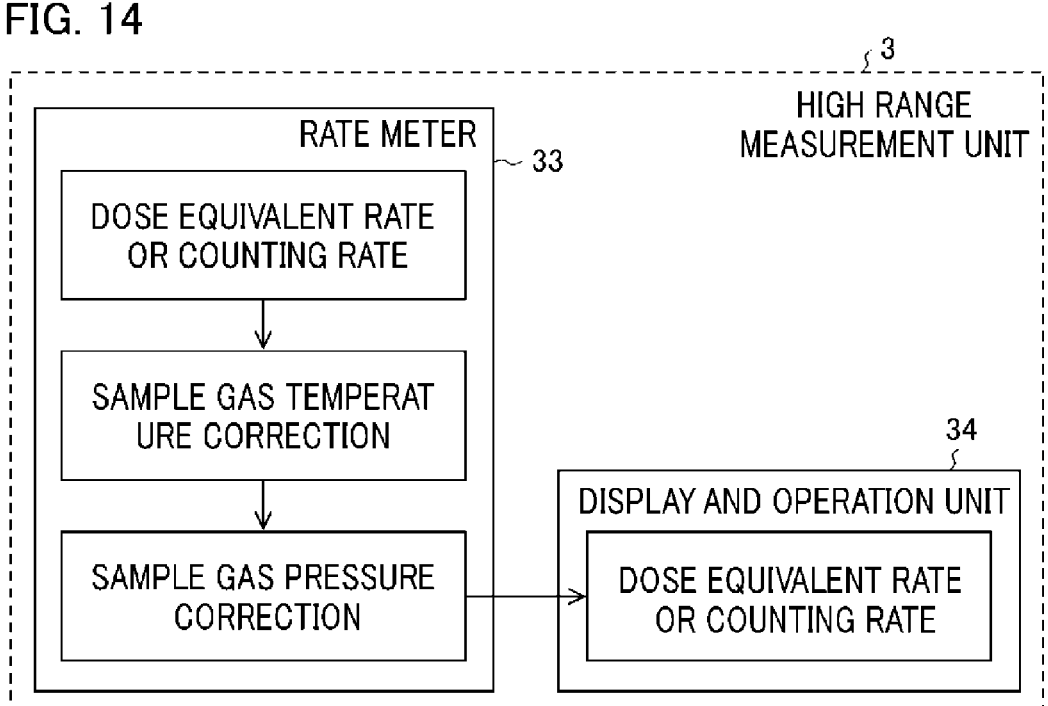
FIG. 14 illustrates a flowchart of an operation in a high range measurement unit of the radioactive gas monitor according to Embodiment 5 of the present invention.

FIGS. 13 and 14 illustrate a flowchart of an operation in the low range measurement unit 2 and the high range measurement unit 3 of the radioactive gas monitor according to Embodiment 5. FIG. 14 illustrates the high range measurement unit 3 (refer to FIG. 4) according to Embodiment 1 described above. However, the high range measurement unit 4 (refer to FIG. 10) according to Embodiment 2 described above also has the same configuration.

The low range measurement unit 2 and the high range measurement unit 3 are respectively configured so that the rate meters 23 and 33 are provided with a sample gas temperature correction function and a sample gas pressure correction function. The sample gas temperature correction function converts the engineering value into the reference temperature, based on the input sample gas temperature. The sample gas pressure correction function converts the temperature-corrected engineering value into the reference pressure, based on the sample gas pressure. The display and operation units 24 and 34 display the counting rate or the dose equivalent rate, for example, as the engineering value which is temperature-corrected and pressure-corrected.

According to Embodiment 5, an advantageous effect which is the same as those in Embodiment 1 to Embodiment 4 can be obtained. The engineering value corresponding to the radioactive concentration is output by being automatically temperature-corrected and pressure-corrected. Therefore, there is an advantageous effect in that the operation is simplified.

Embodiment 6

In Embodiment 6 of the present invention, in the radioactive gas monitor according to Embodiment 1 or Embodiment 2 described above, a detector temperature sensor 124 is attached to the radiation sensor 121 of the columnar scintillation detector 12. In addition, in the radioactive gas monitor according to Embodiment 2 described above, a detector temperature sensor 174 is attached to the radiation sensor 171 of the fibrous scintillation detector 17.

Figure 15:
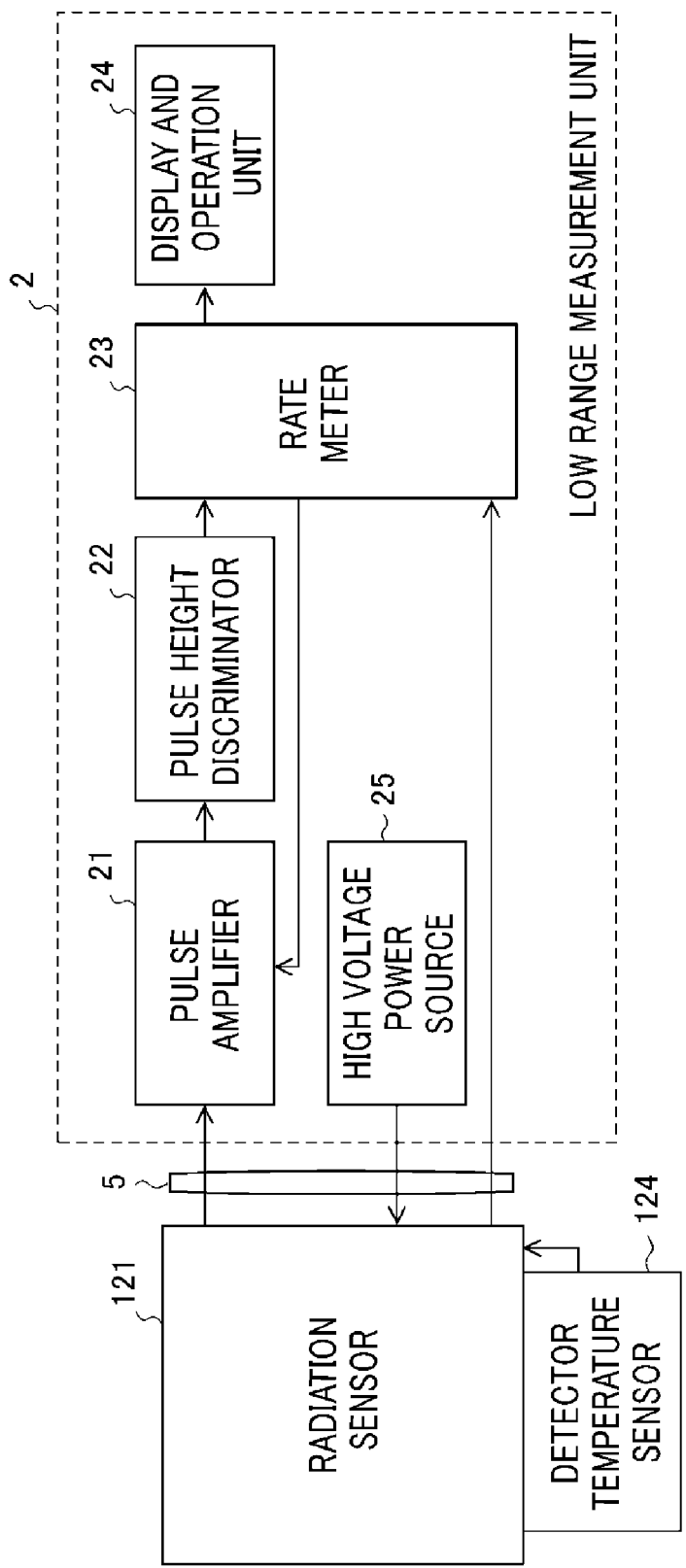
FIG. 15 illustrates a radioactive gas monitor according to Embodiment 6 of the present invention.

As illustrated in FIG. 15, a temperature signal is input to the rate meter 23 of the low range measurement unit 2 from the detector temperature sensor 124 attached to the radiation sensor 121 of the columnar scintillation detector 12. The rate meter 23 performs temperature compensation on the engineering value corresponding to the radioactive concentration, based on the temperature signal.

Figure 16:
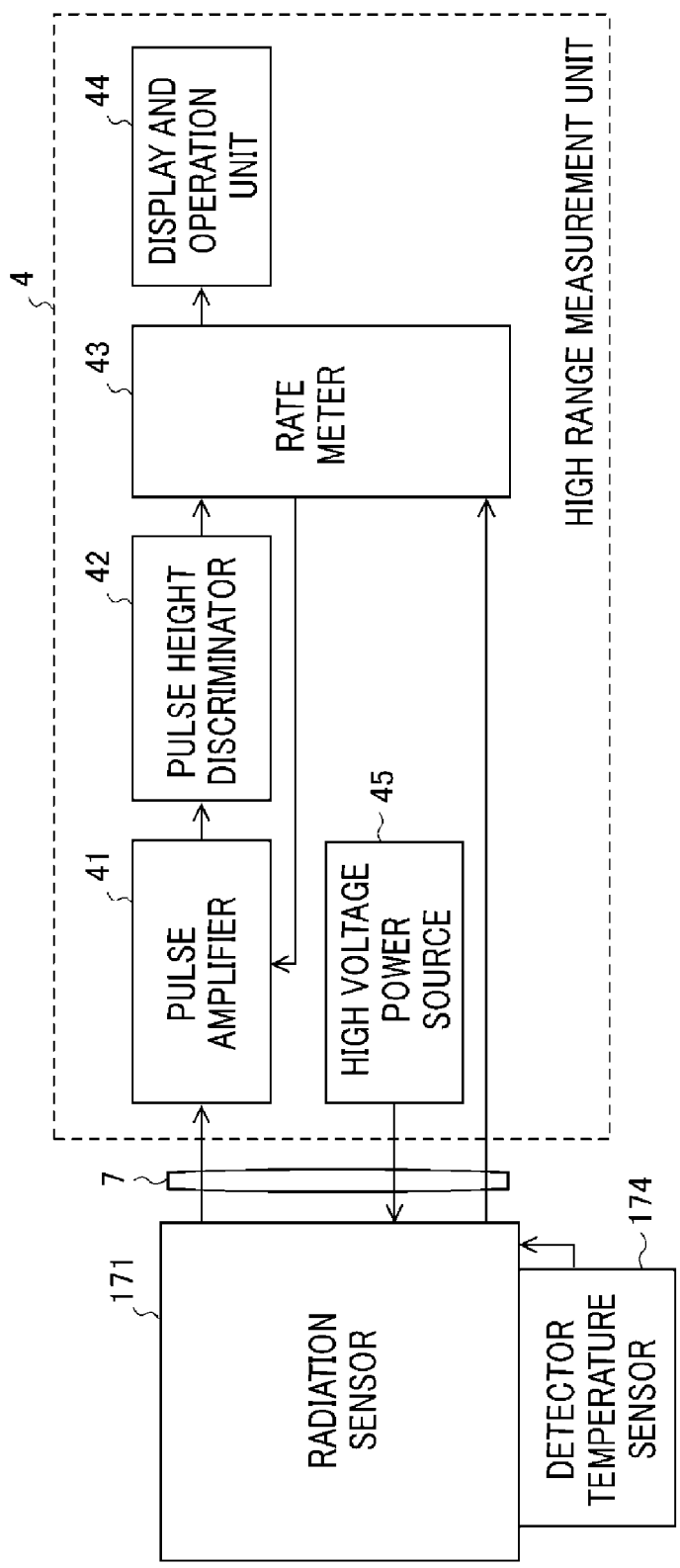
FIG. 16 illustrates the radioactive gas monitor according to Embodiment 6 of the present invention.

As illustrated in FIG. 16, a temperature signal is input to the rate meter 43 of the high range measurement unit 4 from the detector temperature sensor 174 attached to the radiation sensor 171 of the fibrous scintillation detector 17.

The respective rate meters 23 and 43 calculate the temperature based on the input temperature signal. Furthermore, with reference to a temperature compensation table as illustrated in FIG. 17, the respective rate meters 23 and 43 perform temperature compensation on the engineering value corresponding to the radioactive concentration by using a gain compensation counting rate corresponding to the respective temperatures.

According to Embodiment 6, in addition to an advantageous effect which is the same as those in Embodiment 1 and Embodiment 2 which are described above, it is possible to reduce the influence of the temperature during the measurement, thereby improving measurement accuracy. It is also possible to combine Embodiment 6 and Embodiments 3 to 5 described above with each other. Within the scope of the invention, the present invention can be made by freely combining the respective embodiments, or by appropriately modifying and omitting the respective embodiments.

In addition, in Embodiments 1 to 6 which are described above, the columnar scintillation detector 12 is used as the first detector, and the ionization chamber 13 or the fibrous scintillation detector 17 is used as the second detector. However, the present invention is not limited thereto.

Various modifications and alterations of this invention will be apparent to those skilled in the art without departing from the scope and spirit of this invention, and it should be understood that this is not limited to the illustrative embodiments set forth herein.

What is claimed is:

1. A radioactive gas monitor comprising:
    a detection unit that detects radiation emitted from radioactive nuclides contained in sample gas; and
    a measurement unit that processes a signal transmitted from the detection unit and outputs an engineering value corresponding to radioactive concentration, wherein
    the detection unit has a detection tube through which the sample gas flows, a first detector to which a first concentration measurement range within all required measurement ranges of radiation is allocated, a second detector to which a second concentration measurement range within all required measurement ranges of radiation is allocated, wherein concentrations in the second concentration measurement range are higher than concentrations in the first concentration measurement range, and a shield which shields the detection tube, the first detector, and the second detector from environmental radiation,
    the measurement unit has a first measurement unit which processes a signal transmitted from the first detector and a second measurement unit which processes a signal transmitted from the second detector,
    the shield has at least one detector installing hole having a central axis orthogonal to a central axis of the detection tube, and
    at least the first detector between the first detector and the second detector is arranged inside the detector installing hole, and an inner diameter of the detection tube and a relative position between the detection tube and the first detector are determined so that the measurement range of the first detector and the measurement range of the second detector are overlapped with each other.

2. The radioactive gas monitor according to claim 1, wherein
    the shield has one detector installing hole, and
    a radiation sensor of a columnar scintillation detector used as the first detector is arranged inside the detector installing hole, and a cylindrical ionization chamber used as the second detector is arranged side by side in parallel with the detection tube.

3. The radioactive gas monitor according to claim 2, wherein
    the second measurement unit includes a logarithmic amplifier which inputs a DC current output from the cylindrical ionization chamber and outputs a voltage by converting the DC current into the voltage proportional to a logarithm of the DC current.

4. The radioactive gas monitor according to claim 2, wherein the columnar scintillation detector has a preamplifier which converts a current pulse output from the radiation sensor into an analog voltage pulse, and the preamplifier is installed outside the shield.

5. The radioactive gas monitor according to claim 2, wherein
a collimator which narrows down radiation incident on the radiation sensor arranged inside the detector installing hole is disposed inside the detector installing hole.

6. The radioactive gas monitor according to claim 2, wherein
a detector temperature sensor is attached to a radiation sensor of the columnar scintillation detector, and
based on a temperature signal input from the detector temperature sensor, the first measurement unit performs temperature compensation on an engineering value corresponding to radioactive concentration.

7. The radioactive gas monitor according to claim 1, wherein
the shield has two detector installing holes arranged so as to oppose each other across the detection tube, and
a radiation sensor of a columnar scintillation detector used as the first detector is arranged inside one detector installing hole, and a radiation sensor of a fibrous scintillation detector used as the second detector is arranged inside the other detector installing hole.

8. The radioactive gas monitor according to claim 7, wherein
the columnar scintillation detector has a preamplifier which converts a current pulse output from the radiation sensor into an analog voltage pulse, and the preamplifier is installed outside the shield.

9. The radioactive gas monitor according to claim 7, wherein
the radiation sensor of the fibrous scintillation detector has a light guide which is optically bonded to a scintillation fiber which is cut to have a predetermined length, and a photomultiplier tube which is optically bonded to the light guide.

10. The radioactive gas monitor according to claim 7, wherein
the fibrous scintillation detector has a preamplifier which converts a current pulse output from the radiation sensor into an analog voltage pulse, and the preamplifier is installed outside the shield.

11. The radioactive gas monitor according to claim 7, wherein
a collimator which narrows down radiation incident on the radiation sensor arranged inside the detector installing hole is disposed inside the detector installing hole.

12. The radioactive gas monitor according to claim 7, wherein
a detector temperature sensor is attached to a radiation sensor of the columnar scintillation detector, and
based on a temperature signal input from the detector temperature sensor, the first measurement unit performs temperature compensation on an engineering value corresponding to radioactive concentration.

13. The radioactive gas monitor according to claim 7, wherein
a detector temperature sensor is attached to a radiation sensor of the fibrous scintillation detector, and
based on a temperature signal input from the detector temperature sensor, the second measurement unit performs temperature compensation on an engineering value corresponding to radioactive concentration.

14. The radioactive gas monitor according to claim 1, wherein
the detection unit includes a sample gas temperature sensor which detects a temperature of sample gas flowing through the detection tube, and a sample gas pressure sensor which detects a pressure of the sample gas flowing through the detection tube, and
the measurement unit obtains a sample gas temperature and a sample gas pressure, based on a temperature signal input from the sample gas temperature sensor and a pressure signal input from the sample gas pressure sensor.

15. The radioactive gas monitor according to claim 14, wherein based on the sample gas temperature and the sample gas pressure, the measurement unit outputs an engineering value corresponding to radioactive concentration by converting the engineering value into a predetermined temperature and pressure.

* * * * *